US007332352B2

(12) United States Patent
Reeve

(10) Patent No.: US 7,332,352 B2
(45) Date of Patent: Feb. 19, 2008

(54) SEPARATION PARTICLES

(75) Inventor: Michael Alan Reeve, Amersham (GB)

(73) Assignee: GE Healthcare Limited, Amersham (GB)

( * ) Notice: Subject to any disclaimer, the term of this patent is extended or adjusted under 35 U.S.C. 154(b) by 1136 days.

(21) Appl. No.: 10/007,327

(22) Filed: Nov. 8, 2001

(65) Prior Publication Data

US 2002/0146848 A1 Oct. 10, 2002

(30) Foreign Application Priority Data

Nov. 9, 2000 (GB) ................................ 0027387.0

(51) Int. Cl.
*G01N 33/553* (2006.01)
*G01N 33/53* (2006.01)
(52) U.S. Cl. ........................ 436/526; 436/518; 435/7.5
(58) Field of Classification Search ................ 436/518, 436/526; 435/7.5
See application file for complete search history.

(56) References Cited

U.S. PATENT DOCUMENTS

| 4,795,698 | A | * | 1/1989 | Owen et al. ................... 435/4 |
| 4,920,061 | A | * | 4/1990 | Poynton et al. ............. 436/526 |
| 5,108,933 | A | * | 4/1992 | Liberti et al. ............... 436/501 |
| 5,256,532 | A | * | 10/1993 | Melnicoff et al. ............. 435/5 |
| 5,374,531 | A | * | 12/1994 | Jensen ....................... 435/7.24 |
| 5,385,822 | A | * | 1/1995 | Melnicoff et al. ............. 435/5 |
| 5,660,990 | A | * | 8/1997 | Rao et al. ....................... 435/6 |
| 5,693,784 | A | * | 12/1997 | Ekenberg ................... 536/25.4 |
| 6,228,624 | B1 | * | 5/2001 | Terstappen ............... 435/173.9 |

\* cited by examiner

*Primary Examiner*—Long V. Le
*Assistant Examiner*—Pensee T. Do
(74) *Attorney, Agent, or Firm*—Yonggang Ji

(57) ABSTRACT

A composition comprising colloidal $Fe_3O_4$ particles coated with streptavidin is disclosed. These particles can be used in a method for separating biotinylated compounds from a solution in which the biotinylated compounds bind to the streptavidin-coated particles which are attracted to a surface by a magnet. Also disclosed is a method for making said streptavidin-coated composition, said method comprising the steps of forming colloidal $Fe_3O_4$ particles by mixing aqueous $FeCl_2$ with aqueous $FeCl_3$, adding aliquots of the mixture to an alkaline solution and adding streptavidin.

7 Claims, 1 Drawing Sheet

SEPARATION PARTICLES

FIELD OF THE INVENTION

The present invention relates to magnetic particles for the separation and manipulation of biological compounds. More particularly, the invention relates to streptavidin-derivatised colloidal $Fe_3O_4$ particles.

BACKGROUND OF THE INVENTION

Many molecular biological methods make use of the capture and solid-phase manipulation of compounds. Such methods include solid-phase DNA sequencing, DNA/RNA hybridisation, separation of polymerase chain reaction (PCR) products, labelling of single-stranded nucleic acid probes, gene assembly, in vitro mutagenesis, yeast artificial chromosome (YAC)-screening, DNA cloning, sequence-specific purification of DNA/RNA binding proteins, cell separation and isolation of bacteria etc.

A number of capture methods rely on the interaction between biotin and biotin-binding proteins such as avidin or streptavidin. Streptavidin is a preferred biotin-binding protein as it has four identical subunits each of which has a high affinity binding site for biotin making it suitable for use in the rapid and efficient isolation of biotin-labelled target molecules. The appropriate biotinylated compounds vary according to the application but include compounds such as double-stranded and single-stranded DNA, RNA, proteins, sugars and lectins.

A popular method for such capture and solid-phase manipulation relies upon the use of streptavidin-coated monodisperse magnetic particles, such as those supplied by Dynal A.S. (Dynabeads™ M-280 Streptavidin) which are highly uniform, superparamagnetic, polystyrene beads coated with a polyurethane layer. The stability of the interaction between biotin and streptavidin enables manipulations such as DNA strand melting, hybridisation and elution to be performed without affecting the immobilisation of the biotinylated compound while the magnetic particles allow separation through exposing the beads to a magnetic field gradient. However, such beads are expensive and cumbersome to produce.

Other methods are known in the art. Thus WO 96/37313 discloses complex magnetically responsive microparticles which can be coated with surface-active molecules, such as streptavidin, to effect separation of biological materials. Similarly, U.S. Pat. No. 5,693,539 describes polymer-coated magnetic particles which may be conjugated to binding moieties such as avidin or biotin for the purification and/or separation of bio-molecules. Biotinylated lipid-coated magnetic nanoclusters bearing avidin surface residues have also been described in the literature for use in affinity capture (Sonti S.& Bose A., Colloids and Surfaces (1997) 8 (4); pp 1999-204). However, as with the DYNABEADS™ M-280 Streptavidin product described above, the preparation of these magnetic particles or nanoclusters is both complex and expensive.

There is therefore a need to provide a simple composition of magnetic particles for the separation and manipulation of biological compounds that can be prepared more readily and more cheaply than the known products.

SUMMARY OF THE INVENTION

In view of the needs of the art, the present invention provides a composition comprising colloidal $Fe_3O_4$ particles coated with a biotin-binding protein.

The present invention further provides a method of immobilising a biotinylated compound comprising incubating said biotinylated compound in solution in the presence of a composition of the present invention.

DETAILED DESCRIPTION OF THE PREFERRED EMBODIMENTS

Figure 1:
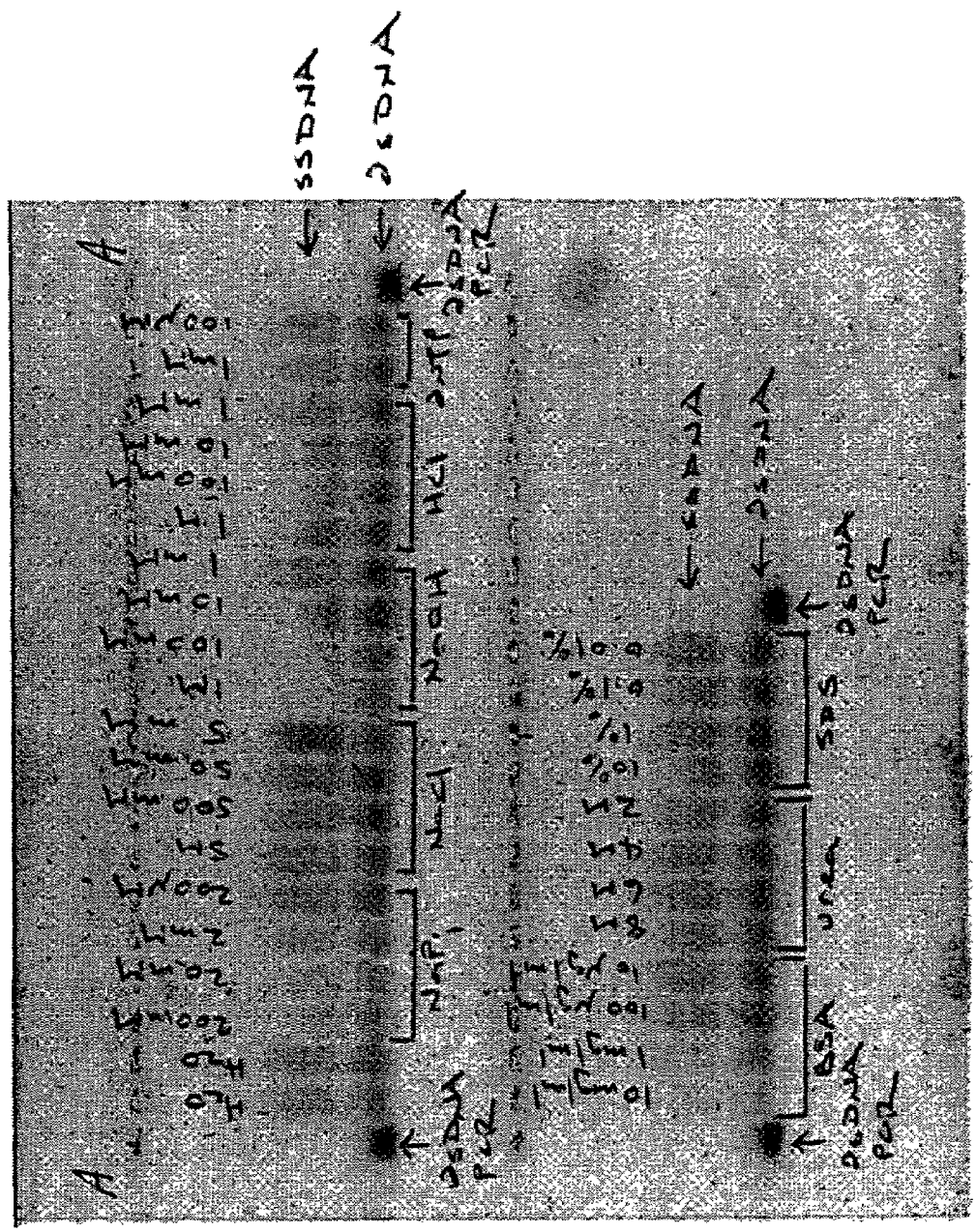
FIG. 1 shows an image of single-stranded and double-stranded PCR products run out on an agarose gel stained with Vistra Green.

Accordingly, in a first aspect of the present invention, there is provided a composition comprising colloidal $Fe_3O_4$ particles coated with a biotin-binding protein. Suitably, the biotin-binding protein is avidin or streptavidin. In a particularly desirable embodiment, the biotin-binding protein is streptavidin.

It has been found that colloidal $Fe_3O_4$ particles can be synthesised and that such particles can be coated with a biotin-binding protein such as streptavidin. Such coated particles have a high iron content (approximately 72%) aiding the speed and efficiency of magnetic separations. They also display excellent performance for the capture and solid-phase manipulation of biotinylated compounds such as biotinylated PCR product strands. Such particles are particularly suitable for automated processes.

Desirably, the $Fe_3O_4$ particles in accordance with the first aspect of the invention are suspended in aqueous solution. Suitably, $Fe_3O_4$ particles may be suspended in water or in an aqueous solution comprising phosphate at a concentration of less than 2 mM or comprising NaOH at a concentration of less than 1 mM. Other suitable aqueous solutions may comprise HCl at a concentration of less than 1 mM, BSA at less than 100 µg/ml, NaCl at less than 5M, dNTP at less than 1 mM, urea at less than 8M or SDS at less than 1%.

The sizes of the particles will be highly dispersed and dependent on the solvent conditions. Particles are at their smallest effective size i.e. most disaggregated after repeated washing in deionised water.

In a second aspect of the invention, there is provided a method for synthesis of a composition in accordance with the first aspect, the method comprising incubating colloidal $Fe_3O_4$ particles with a biotin-binding protein, preferably streptavidin or avidin and, most preferably, streptavidin.

In one embodiment of the second aspect, the method comprises the steps of:

a) forming colloidal $Fe_3O_4$ particles by mixing aqueous $FeCl_2$ with aqueous $FeCl_3$ and adding aliquots of the mixture to an alkaline solution;

b) adding a biotin-binding protein.

In a particularly desirable embodiment, the biotin-binding protein added in step b) is streptavidin.

Suitably aqueous $FeCl_2$ is mixed with aqueous $FeCl_3$ in suitable proportions for the formation of $Fe_3O_4$. In one embodiment, aqueous $FeCl_2$ is mixed with aqueous $FeCl_3$ at a molar ratio of between 1:1.5 and 1:2, $FeCl_2:FeCl_3$, and preferably at a ratio of 1:1.5. In a particularly preferred embodiment, aqueous $FeCl_2$ may be in the form of $FeCl_2.4H_2O$ and aqueous $FeCl_3$ may be in the form of $FeCl_3.6H_2O$. Suitably, the alkaline solution to which the mixture of $FeCl_2$ and $FeCl_3$ is added is an ammonia solution.

The biotin-binding protein is desirably added in excess i.e. to provide an excess of biotin-binding protein compared to the number of available sites that can bind a biotin-binding protein. The number of available binding sites will be dependent on the available surface area of $Fe_3O_4$ particles.

In a third aspect of the invention, there is provided a method of immobilising a biotinylated compound comprising incubating said biotinylated compound in a solution in the presence of a composition in accordance with the first aspect.

Suitable conditions for the binding of proteins such as avidin or streptavidin to biotin will be recognised by those skilled in the art. Preferably, binding of the protein to biotin occurs when the $Fe_3O_4$ particles coated with a biotin-binding protein are incubated with the biotinylated compound at room temperature.

In one embodiment of the third aspect, the biotinylated compound is selected from a nucleic acid molecule, a protein or a peptide. Suitable nucleic acid molecules include double stranded or single stranded DNA, PCR products, oligonucleotides, RNA or PNA. Suitably, a protein or peptide may be an antibody or antibody fragment.

In another embodiment, the biotinylated compound may be a linker compound such as a biotinylated linker arm containing a reactive group at the opposite end to the biotin. Suitable linker compounds include sulfosuccinimidyl-6-(biotinamido)hexanoate (Pierce) and (+) biotinyl-3-maleimidopropionamidyl-3,6-dioxaoctainediamine. The reactive group may subsequently be reacted to allow linkage to another compound, for example, to glutathione or a nickel chelating agent which can, in turn, be bound to a GST- or His-tagged compound.

In a yet another embodiment, the biotinylated compound and the composition are subsequently magnetically attracted to a surface and separated from said solution.

The following examples are for illustration purposes only and should not be used in any way to limit the appended claims.

EXAMPLE 1 a) Synthesis of Colloidal $Fe_3O_4$ Particles 4 g of $FeCl_2.4H_2O$ (Sigma, F-2130, lot #99F3495) were added to 30 ml of water (Elga, Spectrum, >18 MΩ). 20 ml of 1 M HCl (AR/964 26897 pp62) were then added. 8.85 g of $FeCl_3.6H_2O$ (Aldrich, 20,792-6, lot #45469) were finally added to the above with stirring at room temperature until dissolved.

50×1 ml aliquots of the acidified mixed iron chlorides were slowly added to 500 ml of water (Elga, Spectrum, >18 MΩ) containing 25 ml of concentrated ammonia solution (BDH, AnalaR, 10012, lot #7198610M) with constant stirring to give an 8 mg/ml stock of $Fe_3O_4$ in dilute ammonia solution. 250 ml of the 8 mg/ml stock of $Fe_3O_4$ in dilute ammonia solution was allowed to settle under gravity and the supernatant was carefully decanted until the volume was 100 ml (giving a 20 mg/ml $Fe_3O_4$ stock in dilute ammonia solution).

2×50 ml aliquots of the 20 mg/ml $Fe_3O_4$ in dilute ammonia solution were placed in 50 ml Falcon tubes. The $Fe_3O_4$ particles were washed twice with 50 ml of water (Elga, Spectrum, >18 MΩ) using a pair of magnetic Dynal MPC-1 separators (Dynal, product #12001) to give a 20 mg/ml aqueous stock of colloidal $Fe_3O_4$ particles.

b) Streptavidin Coating of Colloidal $Fe_3O_4$ Particles 5 mg of streptavidin (Sigma, S-4762, lot #27H6824) was taken up in 1.92 ml of water to give a 2.6 mg/ml stock (stored at 4° C.). 67 µl of 2.6 mg/ml streptavidin were added to 10 ml of the 20 mg/ml aqueous stock of colloidal $Fe_3O_4$ particles followed by rolling overnight at 4° C.

After overnight incubation, samples were washed twice in 10 ml of water. Particles were then resuspended in 10 ml of water. Particles were stored at 4° C.

EXAMPLE 2

Probing the Linkage Between the $Fe_3O_4$ Particles and Streptavidin to Various Chemical Treatments In order to probe the sensitivity of the linkage between the $Fe_3O_4$ particles and streptavidin to various chemical treatments, the streptavidin-coated colloidal $Fe_3O_4$ particles were pre-treated in 20 µl at 20 mg/ml for 1 hour at 4° C. in the solutions shown in Table 1:

TABLE 1

| Solutions Used for Samples | |
|---|---|
| Sample | Solution |
| 1 | Water |
| 2 | Water |
| 3 | 200 mM phosphate buffer (pH 7.4) |
| 4 | 20 mM phosphate buffer (pH 7.4) |
| 5 | 2 mM phosphate buffer (pH 7.4) |
| 6 | 200 µM phosphate buffer (pH 7.4) |
| 7 | 5 M NaCl |
| 8 | 500 mM NaCl |
| 9 | 50 mM NaCl |
| 10 | 5 mM NaCl |
| 11 | 1 M NaOH |
| 12 | 100 mM NaOH |
| 13 | 10 mM NaOH |
| 14 | 1 mM NaOH |
| 15 | 1 M HCl |
| 16 | 100 mM HCl |
| 17 | 10 mM HCl |
| 18 | 1 mM HCl |
| 19 | 1mM dNTPs |
| 20 | 100 µM dNTPs |
| 21 | 10 mg/ml BSA |
| 22 | 1 mg/ml BSA |
| 23 | 100 µg/ml BSA |
| 24 | 10 µg/ml BSA |
| 25 | 8 M urea |
| 26 | 6 M urea |
| 27 | 4 M urea |
| 28 | 2 M urea |
| 29 | 10% SDS |
| 30 | 1% SDS |
| 31 | 0.1% SDS |
| 32 | 0.01% SDS |

After pre-treatment, the particles were washed twice in 500 µl of water and were then taken up in 100 µl of 20 mM tris-HCl (pH 7.4), 2 mM EDTA (pH 8.0), 2 M NaCl (i.e. at 4 mg/ml) ready for biotin capture of PCR product strands.

PCR Amplification

PCR reactions were carried out as described below:

```
(-40) Forward Strand Primer
=
5' GTTTTCCCAGTCACGACG 3'       (SEQ ID No. 1)
```

```
(-28) Reverse Strand Primer-with
5' biotin (batch number 3-5022-4/4) =
5' biotin-AGGAAACAGCTATGACCAT 3'    (SEQ ID No. 2)
```

Both primers were obtained from MWG Biotech GmbH with biotin labelling of the reverse strand primer by incorporation during synthesis.

target AM =
5'GTTTTCCCAGTCACGACGACCATGGTGCACCTGACTCCTGAGGAGAAGTCTGC (SEQ ID No. 3)

CGTTACTGCCATGGTCATAGCTGTTTCCT 3'

| reaction volume | 100 μl |
| --- | --- |
| (−40) FSP | 5 pmol per reaction |
| (−28) RSP-with 5' biotin | 5 pmol per reaction |
| AM target | 5 fmol per reaction |
| dNTP concentration | 50 μM final |
| 25 mM MgCl$_2$ | 2 μl per reaction |
| units of Taq polymerase | 2 U per reaction |

25 cycles of
97° C. for 1 minute
50° C. for 2 minutes
72° C. for 3 minutes followed by
72° C. for 5 minutes 96×PCR reactions were carried out. After PCR amplification, samples were pooled and 100 μl aliquots were used for biotin capture assay.

Capture and Solid-phase Manipulation of Biotinylated PCR Product Strands

100 μl of the pooled PCR reaction was mixed with an equal volume of 4 mg/ml streptavidin-coated colloidal Fe$_3$O$_4$ particles taken up in 20 mM tris-HCl (pH 7.4), 2 mM EDTA (pH 8.0), 2 M NaCl. The tube was incubated at room temperature for 30 minutes with mixing.

The streptavidin-coated colloidal Fe$_3$O$_4$ particles were then washed with 500 μl of 10 mM tris-HCl (pH 7.4), 1 mM EDTA (pH 8.0), 1 M NaCl. Three more identical washes were performed.

The washed streptavidin-coated colloidal Fe$_3$O$_4$ particles were finally incubated in 100 μl of 0.1 M NaOH for 10 minutes at room temperature to denature double-stranded PCR products. The supernatant was removed and added to 100 μl of 0.5 M HEPES.

Upon completion of the programme, 20 μl aliquots from 200 μl of PCR product single strands were mixed with 10 μl of 50% glycerol AGE loading dye and electrophoresed on a 1.5% agarose gel in 1×TBE.

The gel was stained for 60 min in 500 ml of 1×TBE containing 50 μl of Vistra Green (Amersham, RPN 5786, lot #3163-7).

The stained gel was imaged on a Fluorimager SI (LSRDNT1) with a 488 nm laser, 570 DF 30 filter and a PMT setting of 700 V.

Results

The PCR product single strands prepared from the PCR reactions were run out on a gel next to double-stranded controls in order to assess the yield of single-stranded DNA prepared. Note that double-stranded DNA PCR products (2 μl of 1×PCR reaction) are loaded at ⅕th the amount of the single-stranded DNA PCR products (20 μl of 0.5×PCR reaction). The results of this analysis are shown in the gel image in FIG. 1 in which the top row has dsDNA PCR product (A), samples 1-20, dsDNA PCR product (A) and the bottom row has dsDNA PCR product (A), samples 21-32, dsDNA PCR product (A).

As there is a large difference between the staining efficiency between double-stranded DNA (which stains well), and single-stranded DNA (which stains poorly) with the intercalating agent Vistra Green, some double-stranded DNA carry-over is visible in the gel image. Thus, the double-stranded DNA carry-over appears more marked. Some of this carryover can, however, be accounted for as the surface of the Fe$_3$O$_4$ particles has a high affinity for compounds with phosphate groups and thus will bind PCR products. The binding is reversed by subsequent alkali treatment, whereupon single stranded material of both (+) and (−) sense is released, reanneals, and stains with Vistra Green.

The sensitivity of the linkage between uncoated Fe$_3$O$_4$ particles and streptavidin to various chemical treatments has been investigated. The linkage is found to be sensitive to: phosphate concentrations greater than 2 mM, NaOH concentrations greater than 1 mM, HCl concentrations greater than 1 mM and BSA concentrations greater than 100 μg/ml. The linkage is, however, found to be resistant to: NaCl concentrations up to 5 M, dNTP concentrations up to 1 mM, urea concentrations up to 8 M and SDS concentrations up to 1%.

While the preferred embodiment of the present invention has been shown and described, it will be obvious in the art that changes and modifications may be made without departing from the teachings herein. The matter set forth in the foregoing description and accompanying figure is offered by way of illustration only and not as a limitation. Although a number of embodiments are described in detail in the above examples, the instant invention is not limited to such specific examples. The actual scope of the invention is intended to be defined in the following claims when viewed in their proper perspective based on the prior art.

What is claimed is:

1. A composition consisting of colloidal $Fe_3O_4$ particles coated with a biotin-binding protein.

2. The composition of claim 1, wherein the biotin-binding protein is avidin or streptavidin.

3. The composition of claim 2, wherein the biotin-binding protein is streptavidin.

4. A method of immobilising a biotinylated compound comprising incubating said biotinylated compound in a solution in the presence of the composition as claimed in claim 1.

5. The method as claimed in claim 4, wherein the biotinylated compound is a biotin labeled with a substance selected from the group consisting of a nucleic acid molecule, a protein, and a peptide.

6. The method as claimed in claim 5, further comprising the step of separating the biotinylated compound and the composition from said solution.

7. The method as claimed in claim 6, wherein said separating step further comprises the step of magnetically attracting the biotinylated compound and the composition to a surface.

* * * * *

SEQUENCE LISTING

<160> NUMBER OF SEQ ID NOS: 3

<210> SEQ ID NO 1
<211> LENGTH: 18
<212> TYPE: DNA
<213> ORGANISM: ARTIFICIAL SEQUENCE
<220> FEATURE:

-continued

```
<223> OTHER INFORMATION: SYNTHETIC PRIMER

<400> SEQUENCE: 1
gttttcccag tcacgacg                                                 18

<210> SEQ ID NO 2
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 2
agggaaacag ctatgaccat                                               20

<210> SEQ ID NO 3
<211> LENGTH: 82
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 3
gttttcccag tcacgacgac catggtgcac ctgactcctg aggagaagtc tgccgttact   60
gccatggtca tagctgtttc ct                                            82
```